United States Patent
Teodorczyk et al.

(10) Patent No.: US 7,144,495 B2
(45) Date of Patent: *Dec. 5, 2006

(54) ELECTROCHEMICAL TEST STRIP WITH AN INTEGRATED MICRO-NEEDLE AND ASSOCIATED METHODS

(75) Inventors: Maria Teodorczyk, San Jose, CA (US); Ernest J. Kiser, Los Altos, CA (US); Lorin P. Olson, Scotts Valley, CA (US); Devin McAllister, Marlborough, MA (US); Vadim V. Yuzhakov, San Jose, CA (US); Koon-wah Leong, Sunnyvale, CA (US)

(73) Assignee: Lifescan, Inc., Milpitas, CA (US)

( * ) Notice: Subject to any disclaimer, the term of this patent is extended or adjusted under 35 U.S.C. 154(b) by 241 days.

This patent is subject to a terminal disclaimer.

(21) Appl. No.: 10/226,906

(22) Filed: Aug. 23, 2002

(65) Prior Publication Data

US 2003/0150745 A1 Aug. 14, 2003

Related U.S. Application Data

(63) Continuation-in-part of application No. 09/736,788, filed on Dec. 13, 2000, now Pat. No. 6,620,310.

(51) Int. Cl.
*G01N 27/327* (2006.01)
*A61B 5/00* (2006.01)
(52) U.S. Cl. .................. 205/792; 205/775; 600/369
(58) Field of Classification Search ............... 204/400, 204/403.01; 205/775, 792; 422/73; 436/69; 600/369, 365, 347, 368
See application file for complete search history.

(56) References Cited

U.S. PATENT DOCUMENTS 3,699,437 A 10/1972 Amiram (Continued)

FOREIGN PATENT DOCUMENTS

EP 0974840 A2 1/2000

(Continued)

OTHER PUBLICATIONS

European Search Report, Application No. 01 987 292.8 (4 pages) dated Jul. 9, 2004.

(Continued)

*Primary Examiner*—Alex Noguerola (57) ABSTRACT

Methods and devices for electrochemically detecting a change in the viscosity of a fluid are provided. In the subject methods, a fluid sample (e.g., a whole blood sample) is introduced into an electrochemical test strip's electrochemical cell using a micro-needle integrated into one of oppositely spaced apart working and reference electrodes. An electric potential is applied to the electrochemical cell to first achieve a steady state cell current. A decrease in the steady state cell current is then detected and related to a change in viscosity of the sample. In many embodiments, the sample is blood and the change in viscosity is related to the onset of coagulation in the blood sample, and often the PT of the blood sample. An electrochemical test strip includes an electrochemical cell and an integrated micro-needle. The electrochemical cell includes oppositely spaced apart working and reference electrodes and a reagent mixture (e.g., a redox couple and a coagulation catalyzing agent). The micro-needle is integrated into one of the working and reference electrodes of the electrochemical cell.

11 Claims, 5 Drawing Sheets

U.S. PATENT DOCUMENTS

| | | | |
|---|---|---|---|
| 4,849,340 | A | 7/1989 | Oberhardt |
| 5,300,779 | A | 4/1994 | Hillman et al. |
| 5,447,440 | A | 9/1995 | Davis et al. |
| 5,491,408 | A | 2/1996 | Rousseau |
| 5,554,531 | A | 9/1996 | Zweig |
| 5,628,961 | A | 5/1997 | Davis et al. |
| 5,725,747 | A | 3/1998 | Pinkowski et al. |
| 5,916,522 | A | 6/1999 | Boyd et al. |
| 5,942,102 | A | 8/1999 | Hodges et al. |
| 6,046,051 | A | 4/2000 | Jina |
| 6,060,323 | A | 5/2000 | Jina |
| 6,066,504 | A | 5/2000 | Jina |
| 6,120,676 | A * | 9/2000 | Heller et al. ............. 205/777.5 |
| 6,193,873 | B1 | 2/2001 | Ohara et al. |
| 6,197,494 | B1 | 3/2001 | Oberhardt |
| 6,261,519 | B1 | 7/2001 | Harding et al. |
| 6,338,821 | B1 | 1/2002 | Jina |
| 6,352,630 | B1 | 3/2002 | Frenkel et al. |
| 6,379,324 | B1 | 4/2002 | Gartstein et al. |
| 6,612,111 | B1 | 9/2003 | Hodges et al. |
| 6,620,310 | B1 * | 9/2003 | Ohara et al. ................ 205/792 |
| 6,673,622 | B1 | 1/2004 | Jina |
| 2002/0137998 | A1* | 9/2002 | Smart et al. ................ 600/347 |
| 2003/0018282 | A1* | 1/2003 | Effenhauser et al. ........ 600/583 |
| 2003/0028087 | A1 | 2/2003 | Yuzhakos et al. |
| 2003/0028125 | A1 | 2/2003 | Yuzhakov et al. |
| 2003/0143113 | A2 | 7/2003 | Yuzkakov et al. |
| 2003/0212344 | A1 | 11/2003 | Yuzhakov et al. |
| 2003/0212348 | A1 | 11/2003 | Yuzhakov et al. |

FOREIGN PATENT DOCUMENTS

| | | |
|---|---|---|
| EP | 1174078 A2 | 1/2002 |
| GB | 1 299 363 | 12/1972 |
| WO | WO 95/06868 A2 | 3/1995 |
| WO | WO 9700441 A | 1/1997 |
| WO | WO 97/18464 A1 | 5/1997 |
| WO | WO 97/18465 A2 | 5/1997 |
| WO | WO 99/47907 A1 | 9/1999 |
| WO | WO 00/06761 A1 | 2/2000 |
| WO | WO 00/74763 A2 | 12/2000 |
| WO | WO 00/74764 A1 | 12/2000 |
| WO | WO 00/74765 A1 | 12/2000 |
| WO | WO 00/74766 A1 | 12/2000 |
| WO | WO 01/72220 | 10/2001 |
| WO | WO 01/72220 A1 * | 10/2001 |
| WO | WO 02/48707 | 6/2002 |
| WO | WO 02/49507 | 6/2002 |

OTHER PUBLICATIONS

European Search Report, Munich, Germany Jun. 17, 2005, re: Application 01 987 292.8.

Austrian Search Report, Vienna, Austria Jun. 17, 2005, re: Singapore Application 200304829-5.

English Abstract of Japanese Publication JP2000185034 dated Jul. 4, 2000 with drawings.

Letter from China Patent Agent (H.K.) Ltd. dated Apr. 4, 2006 with First Office Action from Patent Office of the People's Rupublic of China, Beijing, China, Mar. 3, 2006.

English Abstract and Drawings for CN 1243248, Matsushita Electric Industry Co. Ltd.

English abstract and drawings of Japanese Patent JP2000185034, Jul. 4, 2000, Kawahara Nobuaki, Nageo Takua, "Blood Sampling Needle, its Manufacture, Blood Sample Analysis Device, and its Manufacture".

English abstract and drawings of Soviet Union Patent SU 1805973, Mar. 30, 1993, Anatolij M. Kokarev, "Device for Electrochemical Oxidizing Blood".

English abstract and drawing of European Patent No. EP0031830, Jul. 15, 1981, Paul Gyger, Hugo Schar, "Apparatus for Severing a Fibre Layer of Staple Fibres".

European Search Report, The Hague, Netherlands, Sep. 15, 2005, re European Application No. 03255247.3

* cited by examiner

ELECTROCHEMICAL TEST STRIP WITH AN INTEGRATED MICRO-NEEDLE AND ASSOCIATED METHODS

INTRODUCTION

This application is a continuation-in-part of application Ser. No. 09/736,788 filed Dec. 13,2000, now U.S. Pat. No. 6,620,310, which is incorporated herein by reference in its entirety and to which priority is claimed.

FIELD OF THE INVENTION

The field of this invention is coagulation, and particularly coagulation testing.

BACKGROUND

Coagulation is defined as a transformation of a liquid or sol into a soft, semi-solid or solid mass. Blood naturally coagulates to form a barrier when trauma or pathologic conditions cause vessel damage. There are two well-recognized coagulation pathways: the extrinsic or thromboplastin-controlled and the intrinsic or prothrombin/fibrinogen-controlled coagulation pathway. Both the extrinsic and intrinsic pathways result in the production of thrombin, a proteolytic enzyme that catalyzes the conversion of fibrinogen to fibrin.

Coagulation tests which measure a blood sample's ability to form a clot or coagulate have been developed and used to measure the Prothrombin Time (PT) of a blood sample. Such tests are commonly referred to as PT tests. PT tests find use in a number of different applications. For example, PT tests find use in monitoring patients undergoing anticoagulant therapy. Other situations where PT tests find use include tests to determine: acquired platelet function defect; congenital platelet function defects; congenital protein C or S deficiency; deep intracerebral hemorrhage; DIC (Disseminated intravascular coagulation); factor II deficiency; factor V deficiency; factor VII deficiency; factor X deficiency; hemolytic-uremic syndrome (HUS); hemophilia A; hemophilia B; hemorrhagic stroke; hepatic encephalopathy; hepatorenal syndrome; hypertensive intracerebral hemorrhage; idiopathic thrombocytopenic purpura (ITP); intracerebral hemorrhage; lobar intracerebral hemorrhage; placenta abruption; transient ischemic attack (TIA); Wilson's disease; and the like. As such, PT tests find use in a variety of different applications.

A number of different PT determination tests and devices have been developed. Such devices and test protocols include both optical based devices, such as those described in U.S. Pat. No. 6,084,660; to R. Shartle; and electrochemical based devices, such as those described in U.S. Pat. Nos. 6,046,051; 6,060,323 and 6,066,504; all to A. Jina. In this latter group of patents a device is disclosed which is suitable for electrochemical determination of a change of fluid viscosity in a sample, where the device is characterized by the presence of side-by-side electrodes. This configuration requires the use of relatively large volumes of sample and a measurement protocol that implements a time dependent deconvolution of the background response; i.e., a signal is measured over time and is then distinguished over background. Thus, the protocols employed with Jina's devices are more complicated and perhaps less robust than the protocols used in the present invention described below.

Furthermore, current point-of-care coagulation devices require relatively large samples of blood ($\geq 20$ microliters) to perform a PT assay. To obtain such a large volume of blood, use of a conventional lancet is required. However, the use of conventional lancets can cause pain and trauma to a user and potentially lead to improper compliance with an anticoagulant therapy.

While a number of different PT determination tests and devices have been developed, there continues to be a need for additional protocols and devices. Of particular interest would be the development of PT system that provided for rapid and accurate PT determinations with small sample volumes using inexpensive device components, such as disposable reagent strips. Of even greater interest would be the development of an electrochemical device and protocol that exhibits the above desirable parameters, is suitable for use with small sample volumes, produces minimal pain in a user, and can provide a simple-to-interpret signal that converges to a steady-state value.

Relevant Literature

United States Patent of interest include: U.S. Pat. Nos. 6,084,660; 6,066,504; 6,060,323; 6,046,051; 5,942,102; 5,916,522; 5,628,961; 5,554,531; and 5,300,779. Also of interest are WO 97/18465; WO 95/06868; EP 974840 and GB 1 299 363.

SUMMARY OF THE INVENTION

Methods and devices for electrochemically detecting a change in the viscosity of a fluid (e.g., whole blood) are provided. In the subject methods, a fluid sample is introduced into an electrochemical cell having oppositely spaced apart working and reference electrodes. An electric potential is applied to the cell to first achieve a steady state cell current. A decrease in the steady state cell current is then detected and related to a change in viscosity of the sample. In many embodiments, the sample is blood and the change in viscosity is related to the onset of coagulation in the blood sample, and often the PT of the blood sample. Also provided are test strips, kits thereof and meters for use in practicing the subject methods.

An embodiment of an electrochemical test strip according to the present invention includes an electrochemical cell and an integrated micro-needle. The electrochemical cell includes oppositely spaced apart working and reference electrodes and a reagent mixture (e.g., a redox couple and a coagulation catalyzing agent). In this embodiment of an electrochemical test strip according to the present invention, the micro-needle is integrated into one of the working and reference electrodes.

DESCRIPTION OF THE SPECIFIC EMBODIMENTS

Methods, devices and test strips for electrochemically detecting a change in the viscosity of a fluid are provided. In the subject methods, a fluid sample is introduced into an electrochemical cell having oppositely spaced apart working and reference electrodes. In some embodiments, a micro-needle for obtaining the fluid sample is integrated into one of the working or reference electrodes.

An electric potential is applied to the electrochemical cell to first achieve a steady state cell current. A decrease in the steady state cell current is then detected and related to a change in viscosity of the sample. In many embodiments, the sample is whole blood and the change in viscosity is related to the onset of coagulation in the blood sample, and often the PT of the blood sample. Also provided are electrochemical test strips, kits thereof and meters for use in practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

Methods

As summarized above, the subject invention provides a method for determining a change in viscosity of a fluid sample (e.g., a whole blood sample). Often the subject methods provide a means for determining or detecting an increase in the viscosity of a fluid sample. The subject methods are sufficiently sensitive to detect an increase in viscosity that is less than about 1 cps, and often less than about 0.5 cps in magnitude. As such, the subject methods are sensitive methods for detecting a change in viscosity of a fluid sample.

Another feature of the subject methods is that they are electrochemical methods for determining a change, and often an increase, in the viscosity of a fluid sample. By electrochemical methods is meant that the subject methods employ a working and a reference electrode. Specifically, the subject methods employ a current produced between a working and reference electrode and changes therein to determine a change in viscosity of the fluid sample, as described in greater detail below.

The first step in an embodiment of a method according to the present invention is to introduce a quantity of the fluid to be assayed, i.e., a fluid sample, into an electrochemical cell that includes oppositely spaced apart working and reference electrodes. The nature of the fluid may vary, so long as the fluid is a conductor, e.g., an electrolyte. In many embodiments, the fluid is an aqueous fluid, where of particular interest are physiological samples. Where the fluid is a physiological sample, in many embodiments the fluid is whole blood, or a derivative thereof from which the coagulation/clotting time, and therefore PT time, can be derived.

The amount of fluid, e.g., blood, that is introduced into the electrochemical cell varies, but is generally a small volume. As such, the volume of fluid introduced into the electrochemical cell typically ranges from about 0.1 to 10 µL, usually from about 0.2 to 5.0 µL, and more usually from about 0.3 to 1.6 µL. The sample is introduced into the electrochemical cell using any convenient protocol, where the sample may be injected into the electrochemical cell, allowed to wick into the electrochemical cell, and the like, as may be convenient and depending on the nature of the device/system in which the subject method is practiced. The sample can be introduced into the electrochemical cell using an integrated micro-needle and capillary channel (as described below with respect to the electrochemical test strip of FIGS. 3–5). The use of an electrochemical cell with an integrated micro-needle and capillary channel provides for samples of a unusually small volume in the range of 100 nano-liters to 150 nano-liters to be effectively employed.

While the subject methods may be used, in principle, with any type of electrochemical cell having oppositely spaced apart working and reference electrodes, in many embodiments the subject methods employ an electrochemical test strip. The electrochemical test strips employed in embodiments of the subject invention are made up of two opposing metal electrodes separated by a thin spacer layer, where these components define a reaction area or zone that makes up the electrochemical cell. In other embodiments, the electrochemical strip also includes a micro-needle integrated into either the working electrode or the reference electrode and a capillary channel (see FIGS. 3–5 and their associated description).

Figure 1:
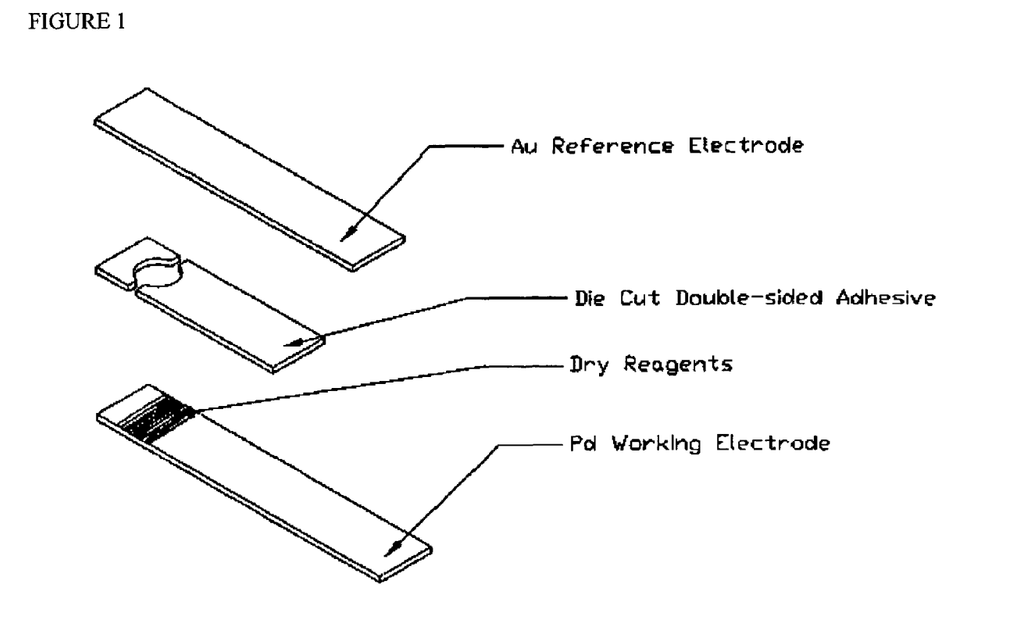
FIG. 1 provides an exploded view of an electrochemical test strip according to the subject invention.
Figure 3:
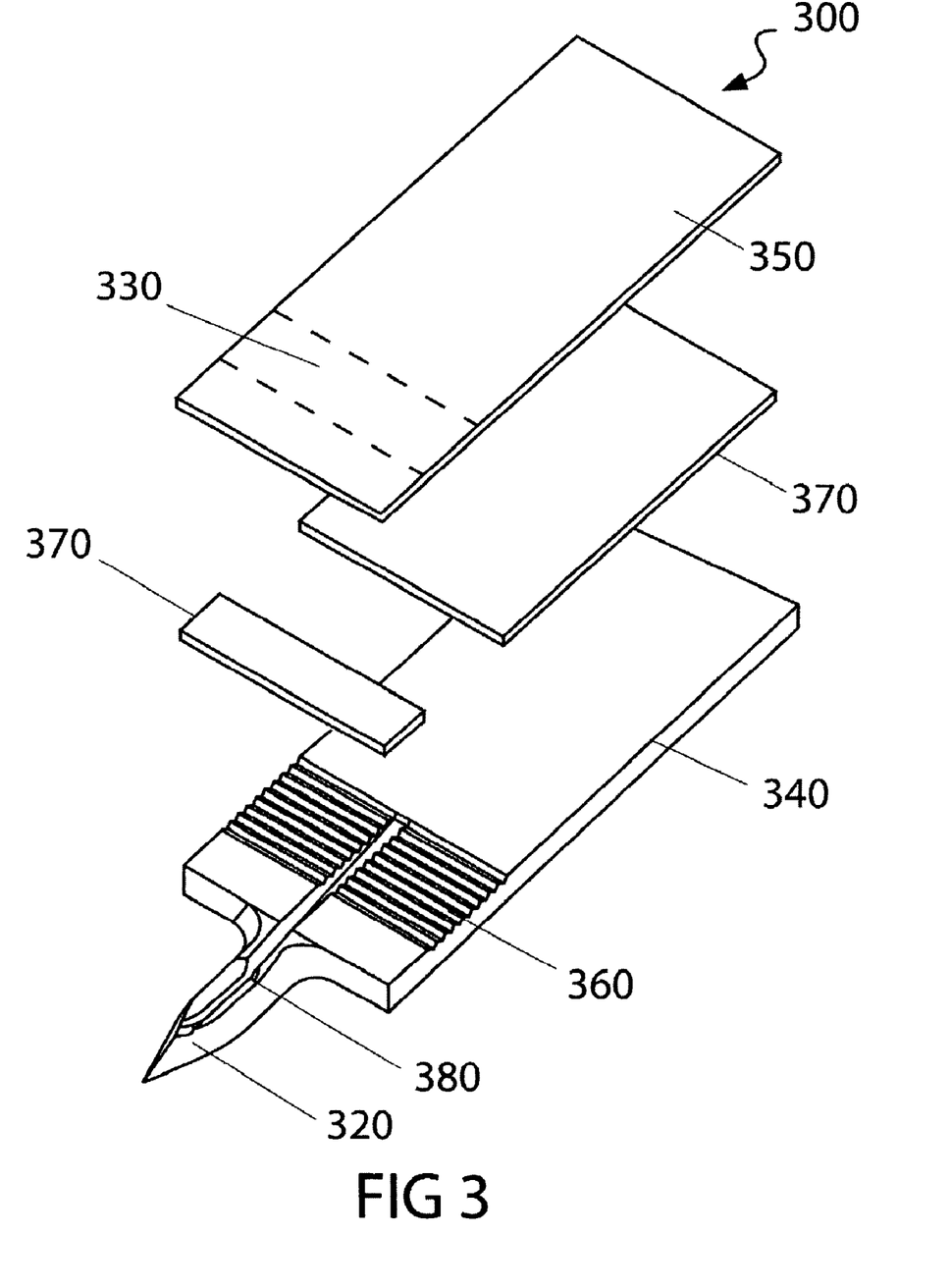
FIG. 3 is a perspective exploded view of an electrochemical test strip with an integrated micro-needle according to the present invention.
Figure 4:
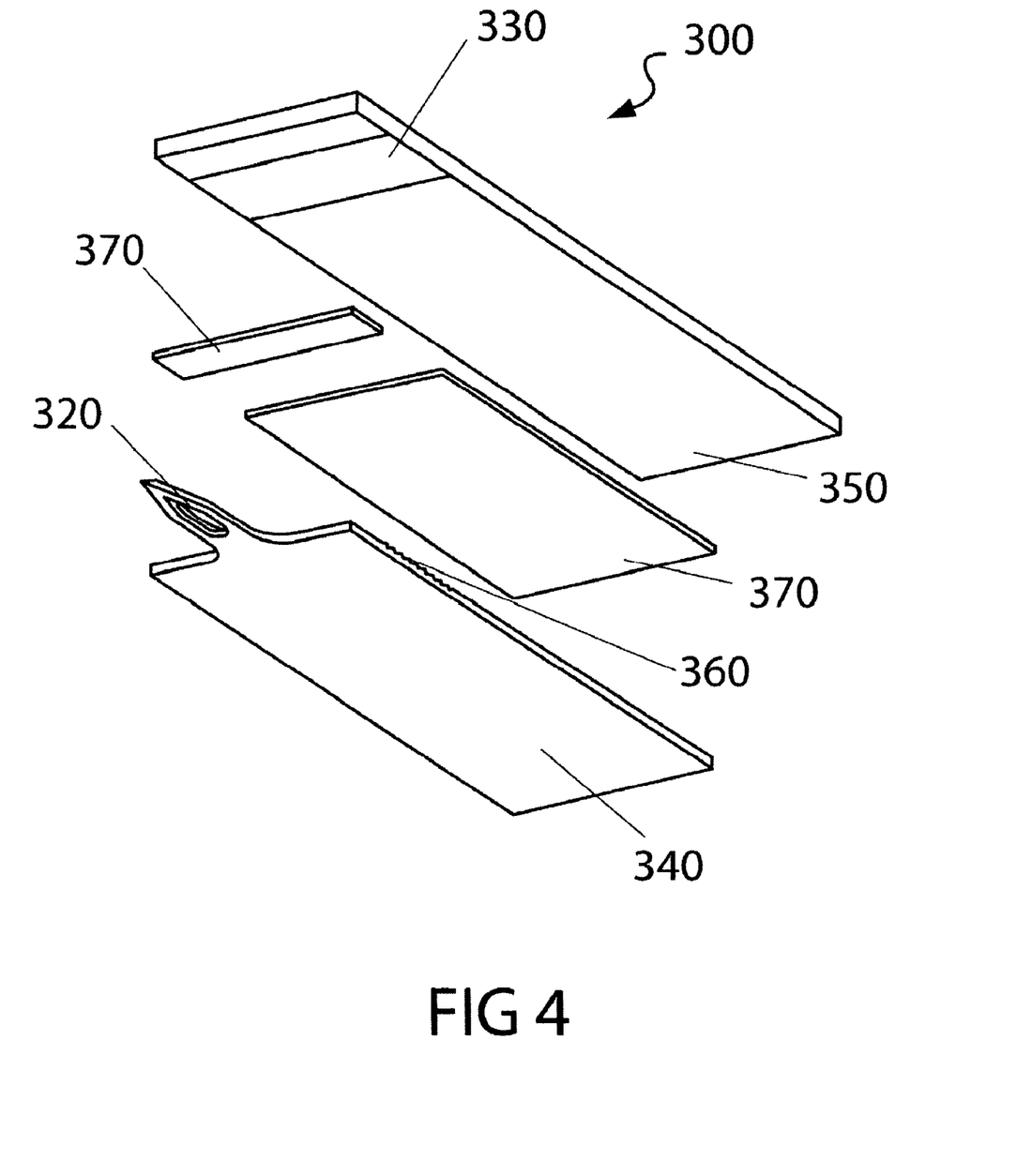
FIG. 4 is a bottom perspective exploded view of the electrochemical test strip of FIG. 3.

In certain embodiments of these electrochemical test strips, the working and reference electrodes are generally configured in the form of elongated rectangular strips. Typically, the length of the electrodes ranges from about 1.9 to 4.5 cm, usually from about 2.0 to 2.8 cm. The width of the electrodes ranges from about 0.07 to 0.76 cm, usually from about 0.24 to 0.60 cm. The working and reference electrodes typically have a thickness ranging from about 10 to 100 nm and usually from about 10 to 20 nm. FIGS. 1, 3 and 4 provide exploded views of electrochemical test strips according to exemplary embodiments of the subject invention.

The working and reference electrodes are further characterized in that at least the surface of the electrodes that faces the reaction area of the electrochemical cell in the strip is a metal, where metals of interest include palladium, gold, platinum, silver, iridium, carbon (conductive carbon ink), doped tin oxide, stainless steel and the like. In many embodiments, the metal is gold or palladium. While in principle the entire electrode may be made of the metal, each of the electrodes is generally made up of an inert support material on the surface of which is present a thin layer of the metal component of the electrode. In these more common embodiments, the thickness of the inert backing material typically ranges from about 25 to 500, usually 50 to 400 µm, e.g., from about 127 to 178 µm, while the thickness of the metal layer typically ranges from about 10 to 100 nm and usually from about 10 to 40 nm, e.g. a sputtered metal layer. Any convenient inert backing material may be employed in the subject electrodes, where typically the material is a rigid material that is capable of providing structural support to the electrode and, in turn, the electrochemical test strip as a whole. Suitable materials that may be employed as the backing substrate include plastics, e.g. PET, PETG, polyimide, polycarbonate, polystyrene, silicon, ceramic, glass, and the like.

A feature of the electrochemical test strips used in these embodiments of the subject methods is that the working and reference electrodes as described above face each other and are separated by only a short distance, such that the distance between the working and reference electrodes in the reaction zone or area of the electrochemical test strip is extremely small. This minimal spacing of the working and reference electrodes in the subject test strips is a result of the presence of a thin spacer layer positioned or sandwiched between the working and reference electrodes. The thickness of this spacer layer may range from 50 to 750 μm and is often less than or equal to 500 μm. The spacer layer is cut so as to provide a reaction zone or area with at least an inlet port into the reaction zone, and generally an outlet port out of the reaction zone as well. The spacer layer may have a circular reaction area cut with side inlet and outlet vents or ports, or other configurations, e.g. square, triangular, oval, rectangular, irregular shaped reaction areas, etc. The spacer layer may be fabricated from any convenient material, where representative suitable materials include PET, PETG, polyimide, polycarbonate, and the like, where the surfaces of the spacer layer may be treated so as to be adhesive with respect to their respective electrodes and thereby maintain the structure of the electrochemical test strip. Of particular interest is the use of a die-cut double-sided adhesive strip as the spacer layer.

The electrochemical test strips used in these embodiments of the subject invention include a reaction zone or area that is defined by the working electrode, the reference electrode and the spacer layer, where these elements are described above. Specifically, the working and reference electrodes define the top and bottom of the reaction area, while the spacer layer defines the walls of the reaction area. The volume of the reaction area typically ranges from about 0.1 to 10 μL, usually from about 0.2 to 5.0 μL, and more usually from about 0.3 to 1.6 μL. As mentioned above, the reaction area generally includes at least an inlet port, and in many embodiments also includes an outlet port. The cross-sectional area of the inlet and outlet ports may vary as long as it is sufficiently large to provide an effective entrance or exit of fluid from the reaction area, but generally ranges from about $9 \times 10^{-4}$ to $5 \times 10^{-3}$ cm$^2$, usually from about $5 \times 10^{-4}$ to $2.5 \times 10^{-3}$ cm$^2$.

In many embodiments, a reagent system is present in the reaction area, where the reagent system interacts with components in the fluid sample during the assay. For example, in embodiments where the subject methods are used to detect a coagulation event, e.g., to measure PT of a sample, the reaction area or zone includes a reagent system that at least includes a redox couple, and often also includes a coagulation catalyzing agent.

The redox couple of the reagent composition, when present, is made up of one or more redox couple agents. A variety of different redox couple agents are known in the art and include: ferricyanide, phenazine ethosulphate, phenazine methosulfate, phenylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes, and the like. In many embodiments, redox couples of particular interest are ferricyanide/ferrocyanide, and the like.

In many embodiments, the reagent composition also includes a coagulation catalyzing agent. By coagulation catalyzing agent is meant one or more components or reactants that participate or interact with components present in the fluid sample, e.g., whole blood, to initiate the clotting process in the blood sample. For PT assays, the coagulation catalyzing agent generally comprises thromboplastin, which thromboplastin may be purified from a naturally occurring source, e.g., an aqueous extract of acetone dried brain tissue, or synthetic recombinant thromboplastin (r-DNA thromboplastin), which generally includes purified recombinant tissue factor protein and a purified artificial lipid component. A representative coagulation catalyzing agent is thromboplastin-XS with calcium sold under the trade name INNOVIN® by Dade International, Miami Fla.

Other reagents that may be present in the reaction area include buffering agents, e.g. citraconate, citrate, malic, maleic, phosphate, "Good" buffers and the like. Yet other agents that may be present include: divalent cations such as calcium chloride, and magnesium chloride; surfactants such as Triton, Macol, Tetronic, Silwet, Zonyl, and Pluronic; stabilizing agents such as albumin, sucrose, trehalose, mannitol, and lactose.

The reagent system, when present, is generally present in dry form. The amounts of the various components may vary, where the amount of the oxidized redox couple component typically ranges from about 5 to 1000 mM, usually from about 90 to 900 mM; the reduced redox couple component typically ranges from about 1 to 20 mM, usually from about 5 to 15 mM; the amount of buffer typically ranges from about 0 to 300 mM, usually from about 50 to 100 mM; and the amount of coagulation catalyzing agent component typically ranges from about 0.005 to 50 mg/cm$^2$, usually from about 0.05 to 5 mg/cm$^2$. The overall mass of dry reagent present in the reaction area or zone in these embodiments generally ranges from about 4 to 700 ng/cm$^2$, usually from about 8 to 350 ng/cm$^2$.

Representative electrochemical test strips for use in the subject methods are depicted in FIGS. 1 and 3–5.

Following sample introduction into the electrochemical cell, a constant electric potential is applied to the cell in a manner sufficient to produce a steady state current between the working and reference electrodes of the cell. More specifically, a constant electric potential is applied between the working and the reference electrodes in a manner that produces a steady state current between the two electrodes. The magnitude of the applied electric potential generally ranges from about 0 to –0.6 V, usually from about –0.2 to –0.4 V. In many embodiments where the electrochemical cell includes a redox couple, as described above, application of the constant electrical potential as described above results in the production of a steady state current described by the following formula:

$$i_{ss} = n2FADC_o/L;$$

where:

is equal to the number of electrons transferred;

F is Faraday's constant, i.e., $9.6485 \times 10^4$ C/mol;

A is the area of the working electrode (cm$^2$);

D is the diffusion coefficient of the ferricyanide ion (cm$^2$/sec), where this coefficient may be determined from Fick's first law, i.e. $J(x,t) = -D \frac{dC_o(x,t)}{dx}$, where j is flux, x is the position from the electrode, and t is time (sec);

$C_o$ is the redox couple concentration (mol/cm$^3$), e.g., the ferrocyanide concentration;

and

L is distance between the electrodes (cm), e.g., the spacer thickness.

The overall time period required to obtain the requisite steady state current, as described above, is relatively short in certain embodiments. In such embodiments, the total amount of time required to obtain the steady state current, i.e., the period from sample entry to the cell to establishment of the steady state current, is less than about 15 seconds, usually less than about 10 seconds; and often ranges from about 4 to 15 seconds.

Figure 2:
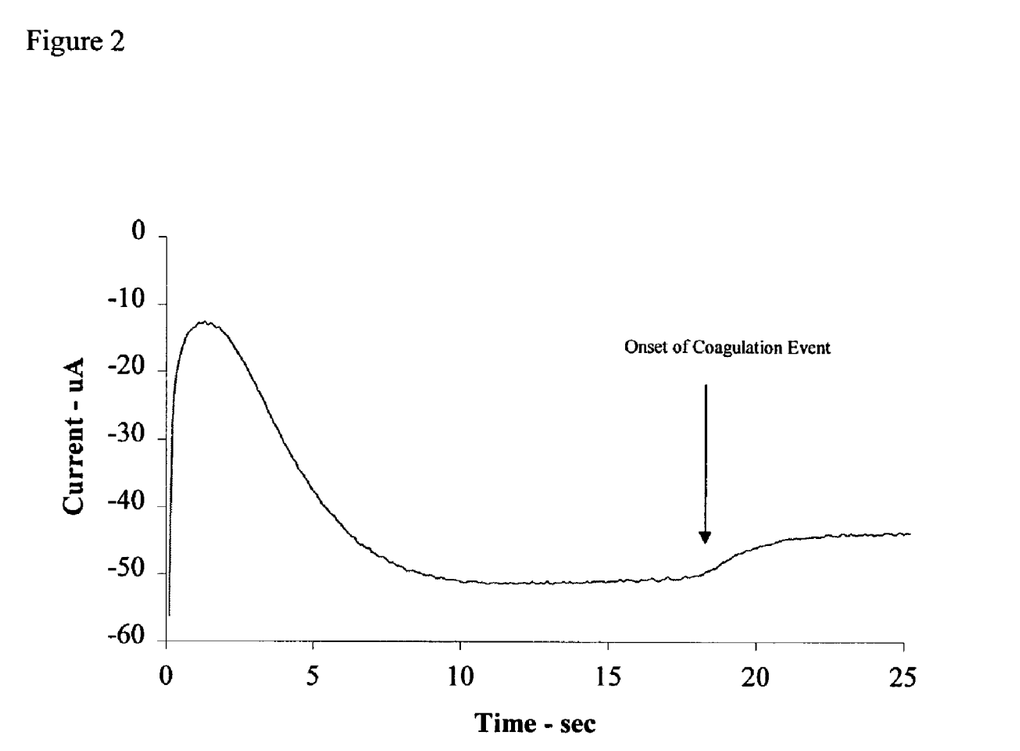
FIG. 2 shows the time-current plot of a typical data set where blood is introduced into an electrochemical test strip and the current is monitored with time.

FIG. 2 shows the time-current plot of a typical data set where blood is introduced into a strip and the current is monitored with time.

The next step in the subject methods is to detect a change in the steady state current and relate this change to a change in viscosity of the sample. In many embodiments, the change that is detected is a decrease in the steady state current. The magnitude of the decrease in the steady state current that is detected in this step is at least about 2%, and usually at least about 10%, where the magnitude of the decrease in many embodiments ranges from about 2 to 90%. In other embodiments, of interest is the rate of change between two steady state values, one before and one after the coagulation event, and the relation of this change in rate to the presence of the coagulation event.

The detection of the above described decrease in steady state current is then related to an increase in viscosity of the fluid sample in the electrochemical cell. Relatively small increases in viscosity result in a detectable decrease in the steady state current and thus can be detected by the subject methods, where the magnitude of the increase in viscosity may be as small as 0.5 cps or smaller in certain embodiments.

In many embodiments where the sample present in the electrochemical cell is whole blood and the reagent composition includes a coagulation catalyzing agent, the increase in viscosity is then related to the onset of coagulation in the blood sample, i.e., the occurrence of a coagulation event or blood clotting in the blood sample.

In certain embodiments, the increase in viscosity and concomitant detection of the onset of coagulation in the blood sample being assayed is employed to determine the PT of the blood sample. In these embodiments, the period extending from the initial sample introduction into the reaction area or zone and/or the establishment of a steady state current and increase in viscosity/onset of coagulation is determined and the PT of the blood sample is derived from this time period. The time at which sample enters the electrochemical cell may be detected using any convenient protocol, where particular protocols employed may depend, at least in part, on the nature of the meter device employed with the electrochemical cell. In certain embodiments, the time that sample is introduced directly into the reaction cell can be manually recorded. Alternatively, the meter may automatically detect sample introduction into the electrochemical cell, e.g., by detecting an initial decrease in the voltage required to achieve a constant current between the working and reference electrodes of the cell. (See U.S. Pat. No. 6,193,873 B1, incorporated herein by reference.) Other protocols for sample detection in the cell may also be employed.

The above computational steps of the subject method, e.g., relation of the time period from sample introduction to onset of coagulation to the PT of the blood sample, may be accomplished manually or through the use of an automated computing means, where in many embodiments the use of an automated computing means, such as is described in connection with the subject devices discussed below, is of interest.

The above described protocol may be carried out at room temperature or at an elevated temperature. Typically, the above protocol is carried out at a temperature ranging from about 20 to 40° C., e.g., about 37° C.

The above described methods find use in any application where the determination of a viscosity change in a fluid sample is desirable. As such, the subject methods suited for use in the determination of PT of a blood sample, and as such find use in any application where the determination of PT is desired, e.g., those applications described in the Background Section, supra.

Electrochemical Test Strips

Figure 5:
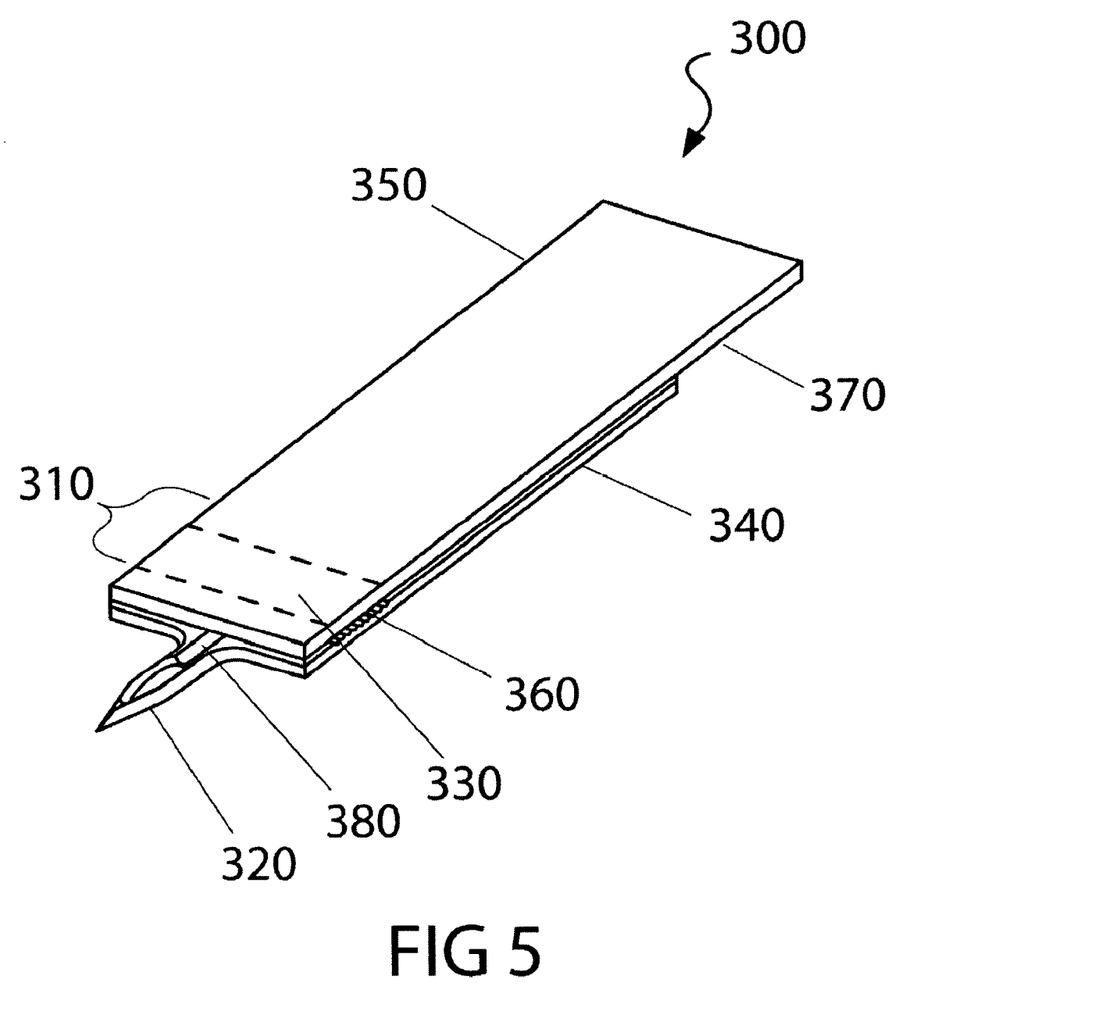
FIG. 5 is a perspective view of the electrochemical test strip of FIG. 3 in an assembled state.

Referring to FIGS. 3–5, an electrochemical test strip 300 according to the present invention includes an electrochemical cell 310, an integrated micro-needle 320 and an integrated capillary channel 380. Electrochemical cell 310 includes a working electrode 350, a reference electrode 340, spreading grooves 360 and a reagent mixture 330.

Working electrode 350 and reference electrode 340 are oppositely spaced apart by divided spacer layer 370. Divided spacer layer 370 serves to define, along with working electrode 350 and reference electrode 340, the boundaries of electrochemical cell 310.

Working electrode 350 and reference electrode 340 can be formed of any suitable material, such as those described above. Reagent mixture 330 (also referred to as a reagent system) includes a coagulation reagent and a redox couple and has also been described above. Reagent mixture 330 can be deposited on one or more of the reference and working electrode by any conventional technique including, for example, spraying, ink jetting and slot coating techniques, but preferably it should be deposited on the working electrode 350.

Integrated micro-needle 320 is adapted for obtaining a whole blood sample from a user and introducing the whole blood sample into the electrochemical cell 310 via integrated capillary channel 380 of electrochemical test strip 300. Once introduced into the electrochemical cell 310, the whole blood sample distributes evenly across spreading grooves 360.

Integrated micro-needle 320 can be manufactured of any suitable material including, for example, a plastic or stainless steel material that has been sputtered or plated with a noble metal (e.g., gold, palladium, iridium or platinum). The shape, dimensions, surface features of the micro-needle, as well as the working penetration depth of the micro-needle into a user's epidermal/dermal skin layer, are configured to minimize any pain associated with obtaining a whole blood sample from the user.

Micro-needles employed in electrochemical test strips according to the present invention can take any suitable form known to one skilled in the art, including those described in U.S. patent application Ser. No. 09/919,981 (filed on Aug. 1, 2001), Ser. No. 09/923,093 (filed on Aug. 6, 2001), Ser. No. 10/143,399 (filed on May 9, 2002), Ser. No. 10/143,127 (filed on May 9, 2002) and Ser. No. 10/143,422 (filed on May 9, 2002), each of which is hereby incorporated in full by reference.

During use of electrochemical test strip 300, a sample (i.e., whole blood) is introduced into electrochemical cell 310 via integrated capillary channel 380 and is distributed evenly within electrochemical cell 310 by spreading grooves 360 when a user's skin is punctured by integrated micro-needle 320. Electrochemical test strip 300 can be employed in methods according to the present invention, as well as in methods according to U.S. patent application Ser. No. 09/736,788 (filed on Dec. 13, 2000), which is hereby incorporated by reference.

In FIGS. 3–5, integrated micro-needle 320 is illustrated as integrated with reference electrode 340. However, once apprised of the present disclosure, one skilled in the art will recognize that integrated micro-needle 320 can be alternatively integrated with working electrode 350.

An advantage of electrochemical test strips that include an integrated micro-needle according to the present invention is a very minimal blood residue following puncture of a user's skin by the integrated micro-needle. In addition, whole blood samples obtained with the integrated micro-needle are simply and effectively transferred directly to the electrochemical cell via the integrated capillary channel. Therefore, there is no need for a user to form a hanging drop of whole blood on the user's skin to conduct a test, thus avoiding difficulties associated with stopping blood flow from a puncture site that has formed a hanging drop of whole blood. In addition, the integrated micro-needles of electrochemical test strips according to the present invention can be adapted to obtain a whole blood sample with a volume in the range of approximately 100 nano-liters (0.1 micro-liters) to 140 nano-liters. Since a direct correlation exists between increased volume of whole blood obtained from a user and an increased sensation of pain, methods and electrochemical test strips according to the present invention provide for reduced pain during use.

Devices

Also provided by the subject invention are meters for use in practicing the subject invention. The subject meters are typically meters for measuring a change in viscosity of fluid sample, and are meters for measuring the PT of a blood sample in many embodiments. The subject meters typically include: (a) a means for applying an electric potential to an electrochemical cell into which the sample has been introduced; (b) a means for measuring cell current in the cell, including a steady state current in the cell; (c) a means for detecting a change in the steady state current in the cell, e.g., a decrease in the steady state current of the cell; and (d) a means for relating the change in steady state current to a change in viscosity of the cell, e.g., a means for relating a decrease in steady state current in the cell to an increase in viscosity of fluid in the cell.

The means for applying an electric potential to the electrochemical cell, means for measuring a steady state current in the cell and means for detecting a change in the steady state current in the cell may be any convenient means, where representative means are described in WO 97/18465 and U.S. Pat. No. 5,942,102; the disclosures of which are herein incorporated by reference. See also U.S. Pat. Nos. 6,066,504; 6,060,323; 6,046,051; the disclosures of which are herein incorporated by reference. The means for relating the change in steady state current to a change in viscosity is typically a computing means present in the meter which is capable of relating the measured change in steady state current to a change in viscosity of the fluid sample. In many embodiments, this means is further a means for relating the change in current/viscosity to the onset of coagulation, and is often a means for determining the PT of a blood sample. See e.g., U.S. Pat. No. 6,066,504; the disclosure of which is herein incorporated by reference.

Kits

Also provided are kits for use in practicing the subject methods. The kits of the subject invention at least include an electrochemical reagent test strip, as described above. The subject kits may further include a means for obtaining a physiological sample. For example, where the physiological sample is blood, the subject kits may further include a means for obtaining a blood sample, such as a lance for sticking a finger, a lance actuation means, and the like. In addition, the subject kits may include a calibration means for calibrating the instrument, e.g., a control solution or standard, e.g., a coagulation control solution that has a known PT time. In certain embodiments, the kits also include an automated instrument, as described above, for detecting the amount of product produced on the strip following sample application and relating the detected product to the amount of analyte in the sample. Finally, the kits include instructions for using the subject kit components in the determination of an analyte concentration in a physiological sample. These instructions may be present on one or more of the packaging, a label insert, containers present in the kits, and the like.

The following examples are offered by way of illustration and not by way of limitation.

EXPERIMENTAL

I. Electrochemical Test Strip Preparation

An electrochemical test strip consisting of two metallized electrodes oriented in a sandwich configuration was prepared as follows. The top layer of the test strip was a gold sputtered Mylar strip. The middle layer was a double-sided adhesive with a punched hole that defined the reaction zone or area. The punched hole was a circle with two juxtaposed rectangular inlet and outlet channels. The bottom layer of the test strip was sputtered palladium on Mylar. A reagent of citraconate buffer, ferricyanide, ferrocyanide and relipidated recombinant tissue factor was ink jetted on the palladium sputtered surface. The amount of reagent ink jetted onto the palladium sputtered surface was 597 ng/cm$^2$. As such, the amount of citraconate buffer was 120 ng/cm$^2$ ferricyanide was 460 ng/cm$^2$, the amount of ferrocyanide was 8 ng/cm$^2$ and the amount of recombinant tissue factor was 9 ng/cm$^2$. An exploded view of the test strip is shown in FIG. 1.

II. Detection of PT

The above described strip is employed to determine the PT of a blood sample as follows. A 1.5 µl blood sample is introduced into the reaction area or zone of the test strip and the sample introduction time is recorded. A constant potential of −0.3 V is applied between the working and reference electrodes, and the resultant current between the two electrodes is monitored. The appearance of a steady state current is first detected, followed by a decrease in the steady state current. The time period from the initial sample introduction to the decrease in steady state current is determined and then related to the PT of the blood sample. FIG. 2 shows the time-current plot of the data set where blood is introduced into a strip and the current is monitored with time.

The above results and discussion demonstrate that subject invention provides a simple and powerful tool to determine the PT of a blood sample. Advantages of the subject methods over non-electrochemical based coagulation detection methods include use of low cost materials and the opportunity to use wide variety of controls, including plasma based controls. Additional advantages of the subject invention include the ability to employ small sample volumes and the fact that the electrochemical measurements made by the subject methods provide a simple-to-interpret signal that converges to a steady-state value. Yet another advantage is the ability to use low cost electrochemical based meters, which provide for significant cost savings. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for detecting a change in the viscosity of a fluid sample, said method comprising:
   (a) introducing a fluid sample into an electrochemical cell of an electrochemical test strip comprising oppositely spaced apart working and reference electrodes, wherein one of the working and reference electrodes includes an integrated micro-needle for obtaining the fluid sample from a user and a capillary channel for introducing the fluid sample from the micro-needle to the electrochemical cell;
   (b) applying an electric potential to said electrochemical cell to produce a steady state current between said oppositely spaced apart working and reference electrodes;
   (c) detecting a change in said steady state current; and
   (d) relating said change in steady state current to a change in viscosity of said fluid sample.

2. The method of claim 1, wherein the introducing step introduces a fluid sample with a volume in the range of 100 nano-liters to 150 nano-liters.

3. The method of claim 1, wherein said fluid sample is a physiological sample.

4. The method of claim 3, wherein said physiological sample is blood.

5. The method of claim 4, wherein said method further comprises relating said change in viscosity to the prothrombin time (PT) of said blood.

6. The method of claim 1, wherein said electrochemical cell comprises a redox couple.

7. A method for detecting the onset of coagulation of a blood sample, said method comprising:
   (a) introducing said blood sample into an electrochemical cell of an electrochemical test strip comprising:
      (i) oppositely spaced apart working and reference electrodes; and
      (ii) a reagent mixture comprising a redox couple;
   wherein one of the working and reference electrodes includes an integrated micro-needle for obtaining the blood sample from a user and a capillary channel for introducing the fluid sample from the micro-needle to the electrochemical cell;
   (b) applying an electric potential to said electrochemical cell to produce a steady state current between said oppositely spaced apart working and reference electrodes;
   (c) detecting a change in said steady state current; and
   (d) relating said change in steady state current to the onset of coagulation in said blood sample.

8. The method of claim 7, wherein said change is a decrease.

9. The method of claim 7, wherein said reagent comprises a coagulation catalyzing agent.

10. The method of claim 9, wherein said coagulation catalyzing agent comprises thromboplastin.

11. The method of claim 10, wherein said method further comprises relating said onset of coagulation to the prothrombin time of said blood sample.

* * * * *